(12) United States Patent
Mutschler et al.

(10) Patent No.: US 10,810,225 B2
(45) Date of Patent: Oct. 20, 2020

(54) SYSTEM AND METHOD FOR LARGE SCALE DATA PROCESSING OF SOURCE DATA

(71) Applicant: The Boeing Company, Chicago, IL (US)

(72) Inventors: Christopher M. Mutschler, Renton, WA (US); Brian K. Predmore, Kent, WA (US); Susan C. Jacintho, Snohomish, WA (US); Nitin L. Gandhi, New Westminster (CA)

(73) Assignee: THE BOEING COMPANY, Chicago, IL (US)

( * ) Notice: Subject to any disclaimer, the term of this patent is extended or adjusted under 35 U.S.C. 154(b) by 653 days.

(21) Appl. No.: 14/643,269

(22) Filed: Mar. 10, 2015

(65) Prior Publication Data

US 2016/0267157 A1   Sep. 15, 2016

(51) Int. Cl.

| | |
|---|---|
| *G06F 16/25* | (2019.01) |
| *G06F 16/2458* | (2019.01) |
| *G06N 5/04* | (2006.01) |
| *G06F 19/00* | (2018.01) |
| *G16H 50/70* | (2018.01) |

(52) U.S. Cl.
CPC ........ *G06F 16/258* (2019.01); *G06F 16/2477* (2019.01); *G06F 19/00* (2013.01); *G06F 19/325* (2013.01); *G16H 50/70* (2018.01); *G06N 5/04* (2013.01)

(58) Field of Classification Search
CPC ......... G06F 17/30569; G06F 17/30551; G06F 19/325; G06F 19/3443; G06F 16/258; G06F 16/2477; G06F 19/00; G06N 5/04; G16H 50/70
See application file for complete search history.

(56) References Cited

U.S. PATENT DOCUMENTS

| | | | | |
|---|---|---|---|---|
| 5,991,714 | A * | 11/1999 | Shaner | G06F 17/2775 704/1 |
| 6,154,636 | A * | 11/2000 | Wright | H04B 7/18506 340/517 |
| 2003/0126056 | A1* | 7/2003 | Hausman | G06Q 10/10 705/36 R |
| 2005/0050068 | A1* | 3/2005 | Vaschillo | G06F 17/30569 |
| 2006/0022048 | A1* | 2/2006 | Johnson | H04W 4/029 235/462.1 |
| 2008/0040152 | A1* | 2/2008 | Vian | G05B 23/0221 705/2 |

(Continued)

*Primary Examiner* — Alford W Kindred
*Assistant Examiner* — Lin Lin M Htay
(74) *Attorney, Agent, or Firm* — MH2 Technology Law Group LLP (57) ABSTRACT

A system and method for processing source data, which includes a translation processor configured on a server to translate a stream of source data received at the server into a stream of formatted data types based on one or more of parameter definitions for the source data and new parameter information for the source data having an unknown data type. The source data can be received at the server from multiple sources and the data format may not be consistent from one source to another. An analytics processor on the server can be configured to operate on the out-of-tolerance data type to perform one or more of trend data analytics, associated data analytics and preventative action analytics.

20 Claims, 8 Drawing Sheets

(56) References Cited

U.S. PATENT DOCUMENTS

| | | | | |
|---|---|---|---|---|
| 2008/0114806 A1* | 5/2008 | Kosche | ............... | G06F 11/3409 |
| 2009/0150412 A1* | 6/2009 | Idicula | ................ | G06F 17/2247 |
| 2009/0254572 A1* | 10/2009 | Redlich | ................. | G06Q 10/06 |
| 2013/0046570 A1* | 2/2013 | Miller | .................... | G06Q 10/00 |
| | | | | 705/7.11 |
| 2014/0358982 A1* | 12/2014 | Pareek | .................... | H04L 67/10 |
| | | | | 709/201 |

* cited by examiner

SYSTEM AND METHOD FOR LARGE SCALE DATA PROCESSING OF SOURCE DATA

BACKGROUND

Field

This invention relates generally to custom computing networks for receiving and processing unstructured source data from sensing devices or computer systems including maintenance, business, health management, or computer system data generated by physical devices and representative of a physical event or "trigger event" and, more particularly, to computing networks configured to process and perform analytics on large amounts of data from multiple sources.

Background

Large scale processing of source data relating to general system health and out-of-tolerance events is becoming an increasing challenge in the management of various system operations, including aircraft system operation and aircraft system maintenance. One of the challenges is processing the increasingly larger scale of the data including what is referred to as "Big Data processing", which is the processing of several petabytes of data.

Large volumes of unstructured data sets from various sources cannot be handled effectively using standard database management techniques using standard computing networks. The challenges can include running large complex computations on datasets searching, organizing storage and, retrieving of pertinent information, efficiently transferring of pertinent information and analysis. The limitations also affect Internet search, finance and business informatics. Data sets grow in size in part because they are increasingly being gathered by ubiquitous information-sensing mobile devices, aerial sensory technologies (remote sensing), software logs, cameras, microphones, radio-frequency identification (RFID) readers, and wireless sensor networks. These types of sensing devices are operational on aircraft systems. The various systems designed to gather source data are not designed to include search functions, storage and retrieval functions, particularly with respect to vital information that may be present in such source data. Vita information (i.e. Vital Data) is intelligence gathered from the source data. Vital data can be data relating to an engine shutdown condition. When managing source data from operational aircraft from various operators, Big Data is difficult to process when using most relational database management systems and desktop statistics and visualization packages. Instead what is required is massive parallel software running on tens, hundreds, or even thousands of servers.

Accordingly, a more effective system is needed for processing very large scale source data in a short period of time, in particular to identify and retrieve vital data.

SUMMARY

The technology as disclosed and claimed herein is a custom configured network tool that automatically receives, processes, categorizes, stores and manages sensor, maintenance, business, health management and other computer systems data received from multiple sources. The tool can scan incoming data for vital data and append the vital data to a data file by means of metadata. Vital data can be data representative of an operating parameter of a physical system where the operating parameter of the physical system is outside of a normal operating range, thus indicative of an out-of-tolerance condition. The vital data is transmitted from the physical system. Alerts and reports can be sent to system user work stations. The tool can categorize and manage the data based on the information contained in the vital data and what source that data came from. The data can be stored and accessed by multiple terminals and users. The technology increases the speed and efficiency of processing very large scale volumes of multiple types of data and data formats. The technology provides a tool for the management and categorization of the vital data, detection and registering of vital data, alerting and reporting relating to the vital data. For example, if oil temperature in an aircraft goes higher than a set threshold, Vital Data will tag that dataset with out-of-tolerance oil temperature condition.

One implementation of the technology is a system for processing source data, which includes a translation processor configured on a server to translate a stream of source data received at the server into a stream of formatted data based on one or more of parameter definitions for the source data and new parameter information for the source data having an unknown data type. The source data is examined and it is determined whether there a known conversion map for translation and if not a conversion map is created.

The source data can be received at the server from multiple sources and the data format may not be consistent from one source to another. For example, aircraft QAR (Quick Access Recorder—airborne flight data recorder designed to provide quick access to raw flight data through a port or wirelessly) data may be received from multiple aircraft operators where each operator may have a fleet of aircraft. One implementation of the technology provides a tool that automatically categorizes and manages the aircraft sensor data, maintenance data and health management data based on one or more of the aircraft type; the operator and the flight data recorder.

Further, a vital data processor on the server can be configured to input the stream of formatted source data into a database and process a trigger function configured to detect event data associated with a physical trigger event. By way of illustration, within the stream of source data, various sensor data can be provided regarding the operation of an aircraft. As an illustration, engine temperature can be provided. If the engine temperature is beyond the range of normal operational temperature, then a trigger event has occurred and the vital data processor can tag the event data as a vital data parameter being out of tolerance. A physical trigger is a representation of a physical system that is operating outside of the normal range, hence a physical trigger. When the event occurs, the system can identify the data as vital data.

In this example, the vital data processor in response to the trigger event can automatically retrieve additional surrounding data that could have a relationship to engine temperature. By way of illustration, the aircraft's altitude may have a direct relationship to the engine temperature and may provide some insight as to why the trigger event occurred. Assessment of the surrounding data can be utilized as a predictive tool or indicator of a pending event. The vital processor can retrieve and store to the database surrounding data, such as aircraft altitude, which is associated with the trigger event and has a predetermined relationship with it. The surrounding trigger data can vary and can be predetermined by the nature of the physical trigger event. Further, an analytics processor on the server can be configured to operate on event data to perform one or more of trend data analytics, associated data analytics and preventative action analytics. The analytics can be based upon the accumulated event data, associated surrounding data and predetermined relationship between the two.

In yet another implementation of the technology, the system can include a monitor processor that is configured to monitor the stream of source data to determine the data type for each dataset within the stream of source data including determining whether the data type is one or more of the following: Sensor Data, Maintenance Data, Business Data, Health Management Data and Computer Systems Data. The monitor processor can also tag the category of data. By way of illustration, if the data had several data types associated to it, the system will tag the data with the correct data types. Additionally, the monitor processor can also determine one or more of the possible values, syntax, the manner in which the data can be stored and possible operation to be performed on the source data.

With the technology as disclosed, the data contained in the stream of source data can be interpreted in order to have a defined format that can be understood and readily manipulated. For example, with aircraft sensor data contained in the source data stream can be detected. In order to accomplish this, a master conversion database can be configured with definitions, a database query function and a comparator operable to determine if a data parameter contained in the stream of source data is a known data type or unknown data type. If it is a known data type, the sensor data can be readily converted and translated for various operations. However, if the data type within the stream of data is unknown, a data definition database can be configured with new definitions to detect the unknown data type.

A further implementation of the technology as disclosed is a method for processing source data, which includes, a translation processor required to translate the source data into a stream of formatted data. The translating can be based on one or more of definitions for the source data and new definitions for the source data having an unknown data type. The technology, as disclosed, can further perform the process of detecting event data with a vital data processor. The process can further include storing to a database tagged event data. Corresponding to the trigger event the method can further perform the process of retrieving and storing to the database surrounding trigger data associated with event data and having a predetermined relationship to the event data. The technology as disclosed can further perform the process of performing on event data one or more of trend data analytics, associated data analytics and preventative action analytics.

In yet a further implementation, the technology can include the process of monitoring the stream of source data with a monitoring processor to determine a data-type. Examples of data types include: Sensor Data, Maintenance Data, Business Data, Health Management Data and Computer Systems Data. Further the process can include determining with a comparator at a master conversion database, if a data parameter contained in the stream of source data is a known data type or unknown data type. The process can also include at a data definition database new definitions for unknown data types. If an unknown data type exists, then a new definition is created by use of a conversion data map.

By way of illustration, a specific implementation of the technology can be processing Quick Access Recorder (QAR) and Flight Data Recorder (FDR) parameter information (sensor data) being provided in a stream of source data to support various incident investigations. The source data can be produced and written in a specific type of format that may be of a known data type or an unknown data type. The technology can be implemented by processors that execute software tools in order to translate the stream of formatted data types into an engineering unit format that is understood and can be consumed by downstream technologies that can analyze the data to determine what is going on onboard the aircraft. However, handling large volumes of data (i.e. several petabytes of data) and the analytics associated with vital data can become a problem. In fact, identifying and handling vital data can be problematic when handling large scale data. The technology as disclosed addresses this problem by processing data, identifying vital data and performing real time analytics. The technology as disclosed supports the automated processing of QAR, FDR, and other data encountered to support Big Data Analytics.

The conversion phase of the technology as disclosed loads the processed and converted data into a large scale data store. The technology further provides for automated analytics or manual analytics that allow for more user interaction with the data and can be implemented in a manner where the technology only processes data that the user needs. For example, the user can analyze only a subset of the information available like computed airspeed and vertical acceleration when analyzing an aircraft. Additionally, the process can execute user defined or automated events. The technology adds value to the source data by the use of the Vital Data Processor. The technology can run prognostic and predictive analysis on the source data and vital data to determine the appropriate maintenance required. For example, if the vital data shown an aircraft engine exceedance on a specific aircraft and the vital data also returns the number of engine exceedance we have had in the past, then the data can be used to determine if the engine needs to be replaced.

By way of illustration, engineering may be interested in glide slope anomalies occurring at specific airports. Glide slope is the trajectory of an aircraft during the landing and approach phase for a specific runway. An engineer may need a subset of sensor data that correlate to the glide slope system. As part of the vital data, the Airport Pairing and a Glide Slope anomaly condition can be registered and associated to the data that was recorded for a flight. The Glide Slope system data is associated with a trigger condition representing the glide slope anomaly therefore the glide slope system data during the landing phase for the airport is required for analysis. Using the present technology an engineer may query the database, and the system can return several days to several years of landings for an airport. The data returned is a subset pertaining to the glide slope system, the glide slope anomaly, and the airport under investigation (all tagged in vital data). An engineer can then load the data into an Analysis Tool. Engineering can now perform data driven analyses to aid in root cause analysis and warranty analysis. Therefore the user can see the alert and also see what else was happening when the alert occurred that may have caused or be related to the trigger event. The user can formulate a fix for the aircraft operator or can use a tool to go and look at other related data for the event.

The technology as disclosed can collect snapshots of all data types (Source Data, Converted Data and Vital Data) and save the data into a large scale data store for advanced analytics which includes trending analysis. Advanced analytics can be based on data that has been recorded and can determine patterns in the data that can initiate additional analytics to be performed. Association of trigger event and the surrounding data is monitored for data integrity and availability.

The technology as disclosed, by way of a representative illustration, can retrieve data from the airline operators and appropriately process the data, run the events and triggers against that data, collect the necessary first order analytics, and make data available to the end users such as engineers and data analyst. The tools of the technology as disclosed can handle data conversion and data storage, such as QAR processing. The technology as disclosed can determine what type of data is contained in the source stream of data and the technology can logically store the source data and work off a copy of the data and preserve the source data. The source data may have been processed in the sense of being categorized and organized, but the data items are in the original format of the source data when stored. The technology can determine if a conversion database is required to convert source data to create a converted data set and determine if a conversion map is available for the source data to convert source data to a correct engineering unit—for example airspeed. In one implementation of the technology the process may retrieve a conversion data map from a customer if no map is available. The technology can be configured to access the master conversion database to determine if parts of the conversion data map can be reused to convert as much as possible from the master conversion database. The parameters that are not logged in the master parameters database can then be logged and found within a data definition database. A new parameter can be created and merged into the master conversion database.

The features, functions, and advantages that have been discussed can be achieved independently in various embodiments or may be combined in yet other embodiments further details of which can be seen with reference to the following description and drawings.

These and other advantageous features of the present invention will be in part apparent and in part pointed out herein below.

BRIEF DESCRIPTION OF THE DRAWINGS

For a better understanding of the present invention, reference may be made to the accompanying drawings in which:

FIGS. 2A1 and 2A2 are an illustration of the process flow for data handling;

While the invention is susceptible to various modifications and alternative forms, specific embodiments thereof are shown by way of example in the drawings and will herein be described in detail. It should be understood, however, that the drawings and detailed description presented herein are not intended to limit the invention to the particular embodiment disclosed, but on the contrary, the intention is to cover all modifications, equivalents, and alternatives falling within the spirit and scope of the present invention as defined by the appended claims.

DESCRIPTION

According to the embodiment(s) of the present invention, various views are illustrated in FIGS. 1-3 and like reference numerals are being used consistently throughout to refer to like and corresponding parts of the invention for all of the various views and figures of the drawing. Also, please note that the first digit(s) of the reference number for a given item or part of the invention should correspond to the Fig. number in which the item or part is first identified.

One embodiment of the present invention comprising a data processing and data analytics tool teaches a novel system and method for a tool that automatically categorizes and manages sensor, maintenance, business, health management and other computer systems data received from multiple sources and performs automated analytics, including one or more of trend data analytics, associated data analytics and diagnosis, introspection, prediction and prognosis.

The details of the invention and various embodiments can be better understood by referring to the figures of the drawing. Referring to FIGS. 1A to 1D, an illustration of the system for data handling and analytics is provided with further detail of the Data Processor elements, and the Data Analytic Processor elements.

Figure 1A:
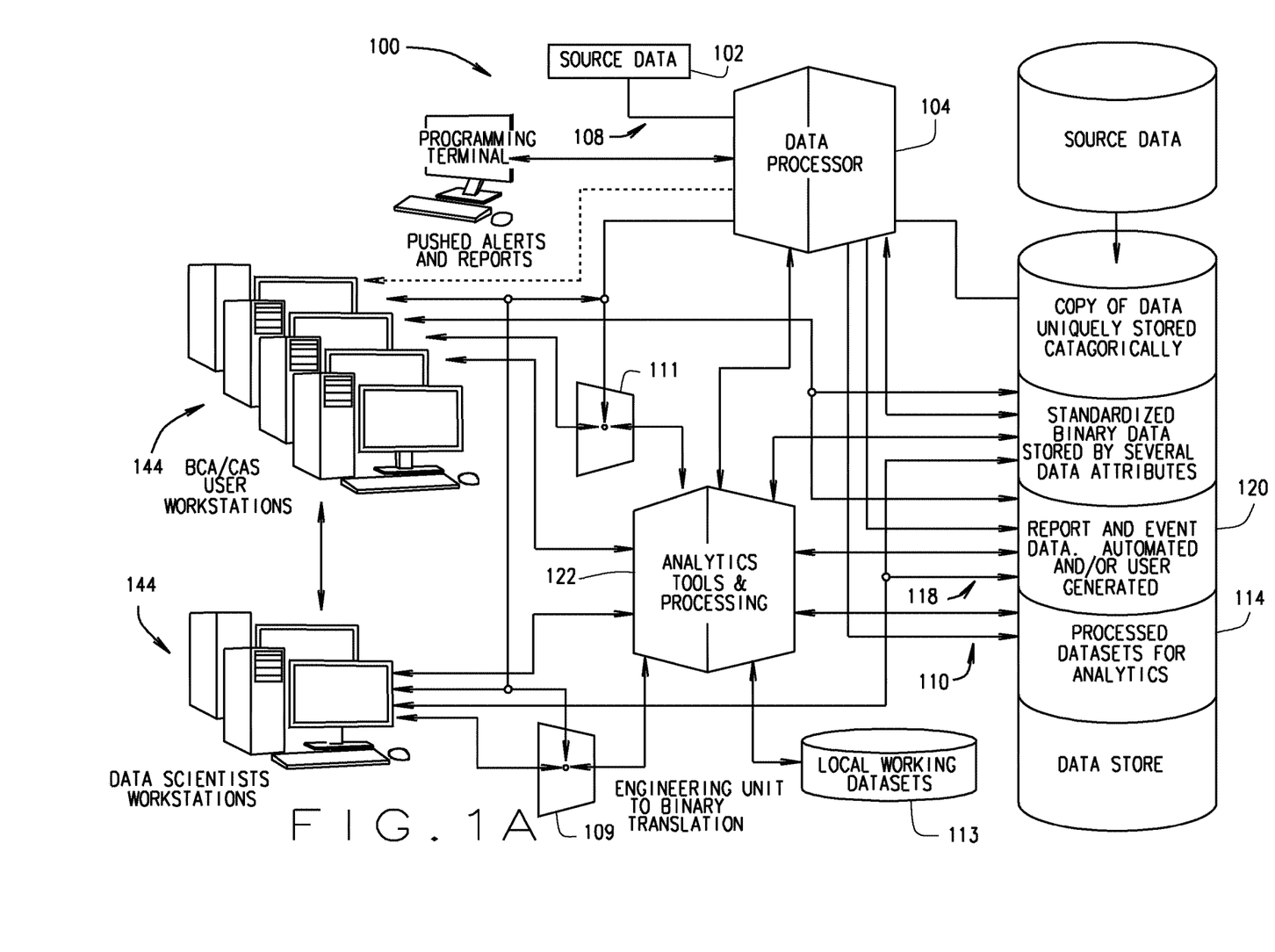
FIG. 1A is an illustration of the system for large scale data handling and analytics.
Figures 1B, 1C:
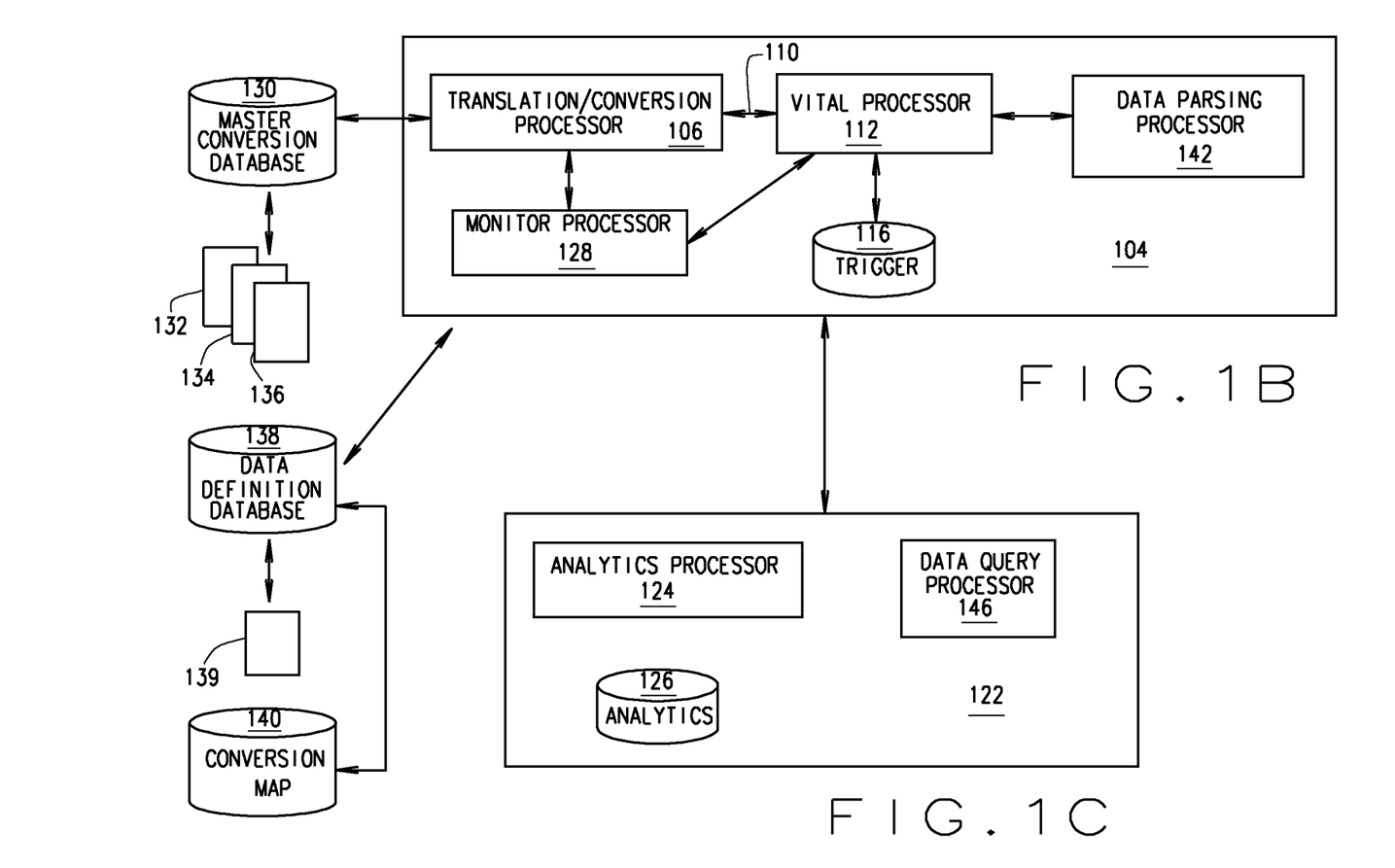
FIG. 1B is an illustration of the Data Processor elements.
FIG. 1C is an illustration of the Data Analytic Processor elements.

Referring to FIGS. 1A and 1B, a system 100 is illustrated for processing source data 102. The system can include a data processing server 104 where a translation processor 106 is configured on the server to translate a stream of source data 108 received at the server into a stream of formatted data types 110 based on one or more of parameter definitions for the source data and new parameter information for the source data having an unknown data type. As shown in FIGS. 1A and 1B, the server 104 can also include a vital data processor 112 where the vital data processor on the server is configured to input the stream of formatted data types 110 contained in the stream of source data 108 into a database 114 and process a trigger function 116 configured to detect a data type considered vital information or "Vital Data."

Vital Data can include, but is not limited to, one or more of Date, Time, Conversion Map, Anomaly Detected, Out Of Tolerance and Trigger Event data detected. Vital Data is associated with and extracted from source data and converted data, and is output to the database 114 as a tagged data type 118 having a tag associated to the vital information. Surrounding data 120 is retrieved and stored to the database 114, where the surrounding data 120 is associated with the vital data and has a predetermined relationship to the vital data. Vital data is generated from source data after running pre-defined algorithms on the source data. The pre-defined algorithms can identify the Vital Data buy using the conversion map as a key to the data content and format. After vital data is generated it is tagged to the source data from which it was generated. So, a tag is an association between these two entities.

Out of tolerance is just a subset of Vital Data. Vital Data is anything that is determined to be useful. For example, airport pairings, date, and time can be vital data because we need to know what each processed file contained. Detecting hard landings on a flight is considered vital data and must be associated to the source data. For example, if the Vital Data is selected by the user to be a specific trigger event, such as an out-of-tolerance reading by a sensor of engine performance, the trigger function 116 outputs the formatted out of tolerance data type 118 to the database 114 having a tag associated to the trigger event, and retrieves and stores to the database surrounding data 120 associated with the trigger event and having a predetermined relationship to the trigger event. A separate analytics server 122 can be utilized or the two servers 104 and 122 can be combined into a single server. An analytics processor 124 on the server can be configured to operate on vital data and converted data to perform analytics 126 including one or more of trend data analytics, associated data analytics and preventative action analytics. Binary data can be translated to engineering units 109 and 111. The analytics processor can operate on local working datasets 113.

Referring to FIG. 1A, the system 100 for processing can further include a monitor processor 128 on the server 104 configured to monitor the stream of source data 108 to determine a data type including determining one or more of sensor data, maintenance data, business data, health management data, and computer systems data. Additionally, and at a more granular level, the system can also detect real, integer, boolean and alphanumeric data types. Vital data is generated from source data after running pre-defined algorithms on the source data. After vital data is generated it is tagged to the source data from which it was generated. So, a tag is just an association between these two entities.

The processor can also be configured to categorize and determine one or more of the possible values, syntax, the manner in which the data can be stored and possible operation to be performed on the source data. The system can further include a master conversion database 130 configured with parameter definitions 132 and a database query function 134 and a comparator 136 operable to determine if a data parameter contained in the stream of source data is a known data type or unknown data type. A data definition database 138 configured with new parameter information 139 and operable to provide the new parameter information for unknown data type to build a conversion map 140.

Figure 1D:
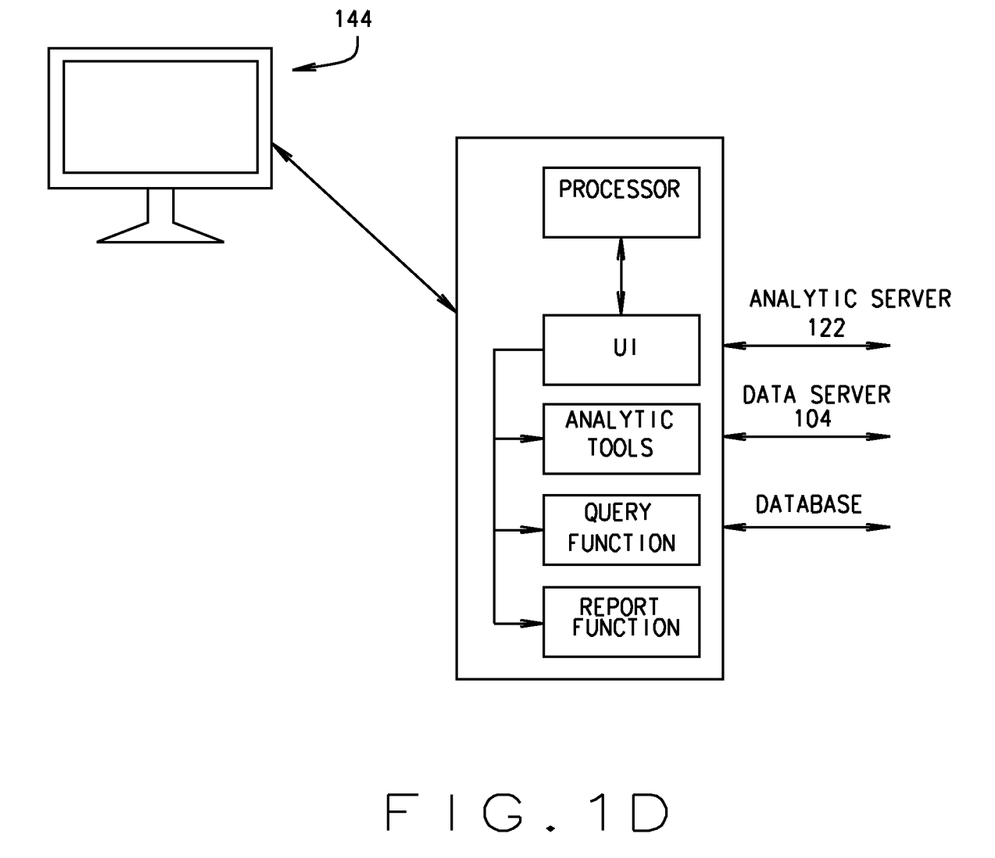
FIG. 1D is an illustration of the User Workstations.

The system 100 for processing data can further include a data parsing processor 142 on the server 104 configured to parse and store the stream of source data in the database 114 based on logical types. The data is parsed based on some logical criteria that fits the data. For example, source data for flights can contain more than 1 flight—legs. The system will first identify the data type as aircraft sensor data and then logically parse out the source data into flight-legs. A computer workstation 144 can be configured to receive analytic results including one or more of trend data analytic results, associated data analytic results and preventative action analytic results and further configured with a user interface configured to present the analytic results. A data query processor 146 may be configured on the server 122 to query and retrieve from the database the tagged event data and the surrounding trigger data 120. The work station 144 can include a processor configured to execute a user interface (UI) to control the analytic tools, query function and report function utilized by the user to access converted and vital data and perform analytics on it.

Referring to FIGS. 2A through 2D an illustration of the process flow 200 for data handling is provided with further illustration for the flow for the data conversion and translation and for the vital processor flow. Data that enters the system is considered Source Data 202. The kinds of data can include but are not limited to Sensor, Maintenance, Business, Health Management, or Computer System data generated by physical devices and representative of a physical event. The data can be in any data standard. When a stream of source data is monitored 203 the Source Data Type can be determined 204 and flagged appropriately and associated to known data types. An undetermined data type can be flagged as unknown. A notification can be issued for further analysis and handling of the data. The stream of Source Data can be managed and stored 205 in a logical manner dependent on data type. An unaltered copy of the Source Data 206 can be preserved in the Source Data Store database.

Referring to FIG. 2A2 a Conversion Data Map 208 can be used that defines the decrypting, aliasing, or unraveling of the stream of source data. The Master Conversion Database is a collection of previously defined data maps and parameters. The Data Definition Database is a collection of parameter properties. The Data Map 208, Master Conversion Database 210, and Data Definitions Database 212 can be used to create a new parameter instances. The Master Conversion Database, which contains definitions of all existing data maps and parameters, is sourced first to determine if the parameter within the incoming Data Map 208 data already exists. The Data Definitions Database, which contains properties for all parameters defined in the Master Conversion Database, is used when a new or unknown parameter is found. For example, a new parameter like Brake Temperature may have never been recorded before, but needs to be recorded for the first time for troubleshooting. The new parameter's definition information is provided to build the new conversion data map. When new parameters are created they are merged with the Master Conversion Database 210. Only new parameters are added to the Master Conversion Database 210; duplicates are not added. All parameters can be processed by Data Conversion/Translation processor 214. The Data Map 208 used by the Data Conversion/Translation processor 214 can be sent to the Vital Data Processor 216 via the Data Conversion/Translation Processor 214. The Data Map used is tagged in the Vital Data for the source data being processed. Once the new parameters have been merged into the Mater Conversion Database, the source data is can now be converted with the new data map.

Figure 2A:
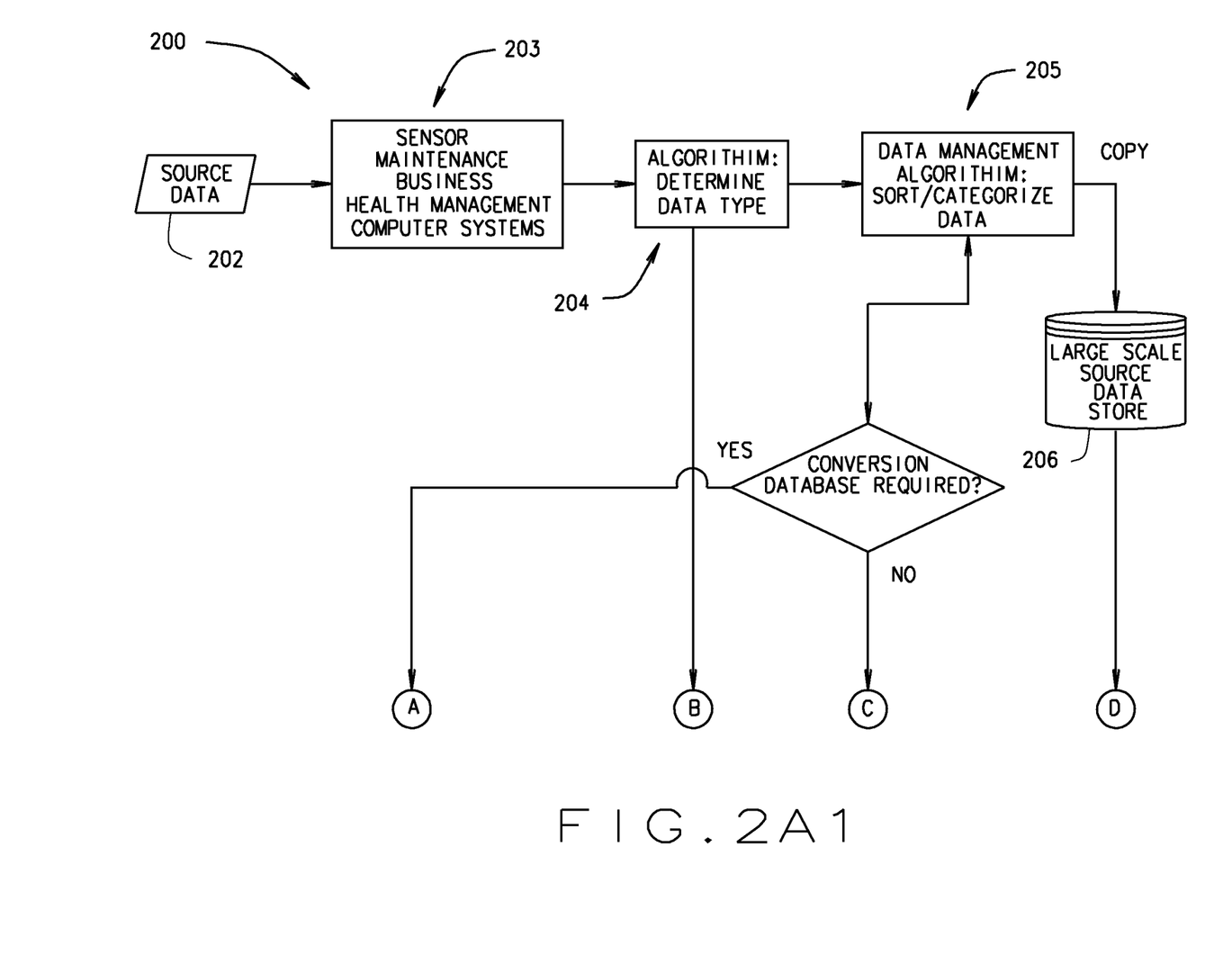
Figure 2A:
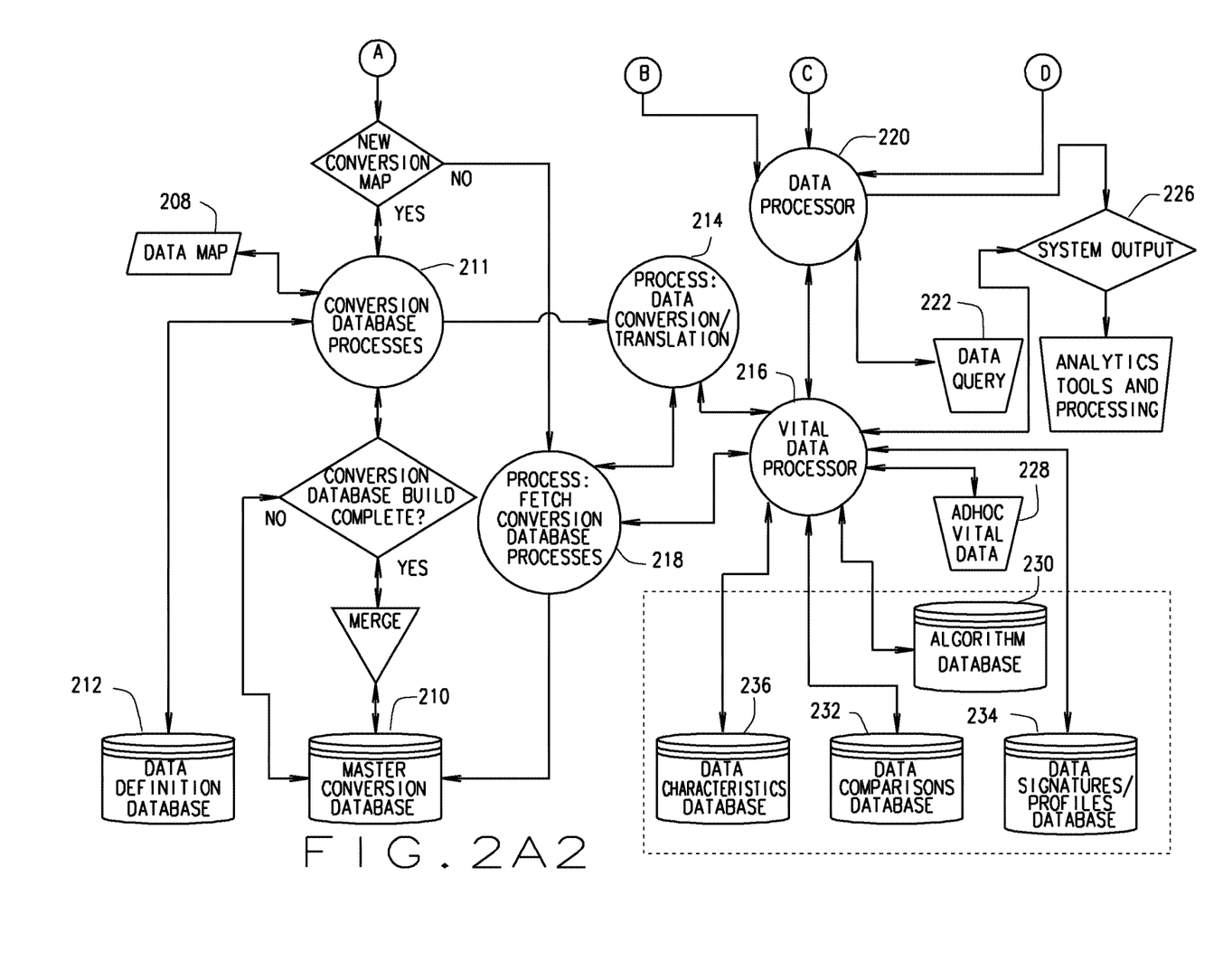

A system notification can be issued when a new parameter is created and sent to the Data Processor 220 via the Data Conversion/Translation Processor 214. An administrative notification can also be issued when a change in the Data Definitions Database has occurred. An administrative notification can also be issued when there is uncertainty or if the new parameter is not found during the Data Definition Database build. The Source Data 202 can be translated into engineering units in its entirety, or it can be translated as a subset via a Data Query 222 from a user.

The fetch conversion database process 218 can receive information regarding the Source Data 202 via the Data Processor 220. The process fetches 218 the parameters and all necessary parameter properties from the Master Conversion Database 210. The process can send the parameter conversion information to the Vital Data Processor 216 and the Data Conversion/Translation processor 214. The Master Conversion Database can be used to obtain the parameter properties required for the Data Conversion/Translation Process 214. The Data Map used in the Data Conversion/Translation Process can be sent to the Vital Data Processor 216 via the Data Conversion/Translation Processor 214. An administrative notification can be issued when there is uncertainty or if the parameter is not found during the Conversion Database build. The Source Data can be translated into engineering units in its entirety, or it can be translated as a subset via a Data Query 222.

In one implementation of the data conversion/translation process 214, the Source Data can be converted to a standard format compatible with the Translation Process. The Data Conversion/Translation Process applies the parameter conversion properties obtained by the Master Conversion Database Process 211 via the Fetch Conversion Database Process 218 to the Source Data.

Figure 2B:
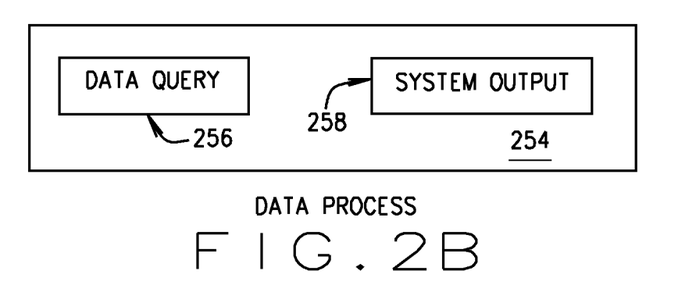
FIG. 2B is a further illustration of the data processing flow.
Figure 2C:
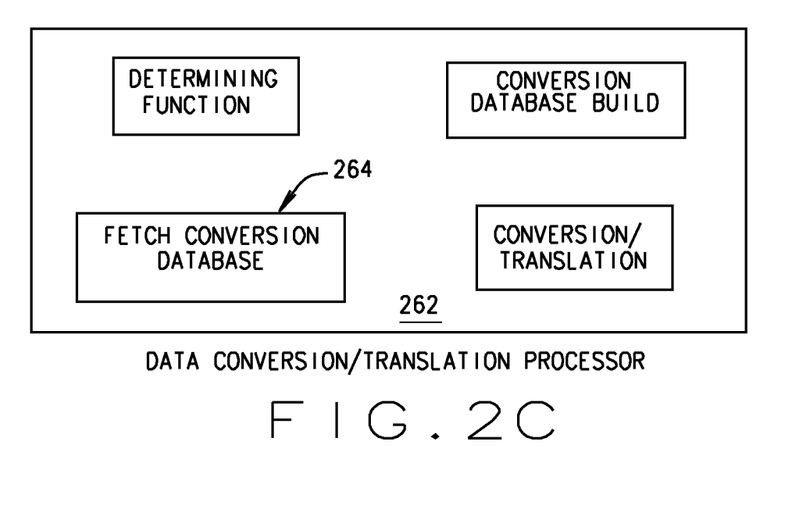
FIG. 2C is a further illustration of the data conversion and translation flow.
Figure 2D:
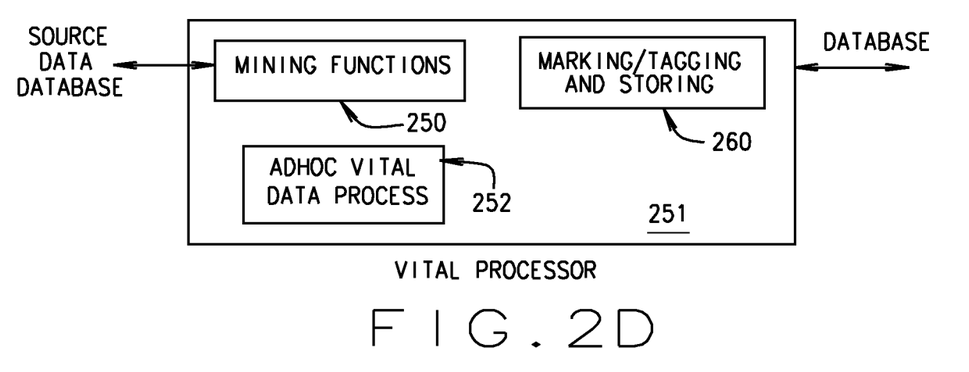
FIG. 2D is a further illustration of the vital processor flow.

The Vital Data Processor can be configured with algorithms from the Algorithm Database 230 to check for Vital Data. The converted Source Data and the Vital Data can be sent to the Data Processor. The Data Processor can receive the translated Source Data from the Data Conversion/Translation Process 262 or the un-translated Source Data (when translation is not required) from the Data Management Algorithm. The Data Processor can also provide a method for obtaining a subset of parameters contained within the Source Data via a Data Query 222. The Data Processor can send the processed data to the System Output 226.

Data Signatures/Profiles Database contains information related to the behavior of a parameter in under certain conditions. Adhoc Vital Data process is a method to inject an algorithm or data signature into the system without storing it in the respective database. Data Comparison database contains business rules to use parameters for analysis. For example, if an aircraft is at cruise the landing gear should be up is an example of a rule across two parameters. Data Characteristics Database is the expected behavior for each parameter. For example, an aircraft with the same configuration travelling to and from the same location should have relatively similar results. The Vital Data Processor 251 is central to this part of the system and connects to the Data Conversion/Transition Process, the Fetch Conversion Database Process 264, the Data Processor, the System Output, the Adhoc Vital Data 252, the Algorithm Database 230, the Data Signatures/Profiles Database 234, the Data Comparisons Database 232, and the Data Characteristics Database 236. The Vital Data Processor can mine the source data to obtain Vital Data. Vital Data can be identified and processed 252 by the Data Type and the applicable Data Characteristics, Data Comparisons, Data Signatures/Profiles, Algorithms, and Adhoc definitions. Vital Data can be processed 252 by a Vital Processor 251 and sent to the Data Processor 254, Data Query 256 and the System Output 258 functions. Vital Data can be marked and stored 260 with the Source Data. Examples of Vital Data can include, but is not limited to, one or more of Date, Time, Conversion Map, Anomaly Detected, and Trigger Event Detected.

In one implementation of the technology an Adhoc Vital Data process can be a method to inject an algorithm, data characteristic, data comparison, or data signature into the system without storing it in the respective database. This adhoc process can be used for testing purposes before promoting a new instance in its respective database. In yet another implementation, the Data Query process can be a method to query specific parameters within the stored Source Data. For example, a user can query aircraft flight sensor data for just a subset pertaining to the Glide Slope System. The parameters that are available within the Source Data can be provided by a user interface. The Data Query can be a subset of the entire parameter set contained within the Source Data. The Data Query is sourced and converted. Multiple source data files can be targeted for parameter extraction. For instance, a user can query years worth of Glide Slope System data that spans over multiple source data files that come from an aircraft.

The Data Definition Database can contain a collection of rules and parameter specifications that are used to create a comprehensive Master Conversion Database. The Data Definition Database can be updated by an external process by means of automation or manual input. If an update occurs, the external process must send a notification to the Conversion Database Process 211. The severity of the change is determined either by manual inspection with engineering judgment or via an automated process. Either process requires user notification that a potential error in a parameter may require corrective action and could impact analysis. Corrective Action is variable, and based on the severity of the discrepancy.

The Master Conversion Database is a collection of parameter conversion definitions developed using the Data Definition Database and the Conversion Data Map. The Master Conversion Database provides a means of standardizing parameter naming convention and describing how each parameter is used relative to the Source Data during conversion. It is under one condition, where a New Conversion Map is required, and where the Master Conversion Database Interfaces with Conversion Database Process. In this process, the parameters in a New Conversion Map are associated with the Source Data. The previously stored parameters are leveraged to so that duplicate parameters do not occur. Data is merged and any duplicates are removed. Notifications are sent if problems are detected. In another condition a New Conversion Map is not required where the Master Conversion Database interfaces with Fetch Conversion Database Process. The parameters are associated with the Source Data and notifications are sent if problems are detected.

By way of illustration, with one implementation of the technology the initial best fit conversion data map can be assigned to airplane manually. The map can be updated when the first change is made to the map via a new map being sent in with the flight data. The system can associate the new map with flight data for this airplane. This data map can continue the association until a new map is sent with new flight data or manually administered. With another implementation, the flight data and data map definition can be transmitted together. The data map can be compared to the last known map. If the map exists, then it can be sent with the flight data to the conversion/translation process. If the map does not exist, the new map can be generated and associated to any flight data that is received after this point until a new map is realized. The data can then be sent to the conversion/translation process. The conversion/translation layer, in the case of Flight Data, can dependent on a data map to unlock the binary bit order for engineering unit conversion.

For data files with synchronization patterns, the data will adhere to the standard sync pattern defined by the specification that created it. For example, Quick Access Recorder Data (QAR) adheres to ARINC 717 format. Therefore, the raw QAR flight data is synchronized to the ARINC 717 Standard.

The Data Characteristic Database contains parameter characteristic information. This information is sent to the Vital Data Processor. For example, an aircraft with the same configuration travelling to and from the same location should have relatively similar results. The Data Characteristics Database can be updated by an external process by means of automation or manual input. Either process requires user notification that a new Data Characteristic Model has been added and available to run against previously stored data. Errors are reported via notification through the Vital Data Processor.

The Data Comparisons Database contains rules to compare parameters. For example, if an aircraft is at cruise the landing gear should be up is an example of a rule across two parameters. This information can be sent to the Vital Data Processor. The Data Comparison Database can be updated by an external process by means of automation or manual input. If an update occurs, the external process must send a notification to the Vital Data Processor. Either process requires user notification that a new Data Comparison Model has been added and available to run against previously stored data. Errors are reported via notification through the Vital Data Processor.

The Data Signature Profile Database contains information related to the behavior of a parameter in under certain conditions. It represents the typical expected behavior of a parameter under a specific set of conditions. For example, if the brake pressure is lower than the required pressure needed to stop an aircraft then there is a larger impact on the speed brakes. Similarly if the speed brakes are under used then more breaking is required to slow the airplane down resulting in high brake temperature. A given parameter can have multiple Data Signature Profiles, depending on the number of applicable conditions necessary to fully describe the parameter's expected behavior. A Data Signature Profile can be extremely complex, and can be a function of multiple parameters. This information is sent to the Vital Data Processor. The Data Signature Database is updated by an external process by means of automation or manual input. If an update occurs, the external process sends a notification to the Vital Data Processor. Either process requires user notification that a new Data Signature Model has been added and available to run against previously stored data. Errors are reported via notification through the Vital Data Processor.

Unaltered Source Data and its associated Vital Data are archived in the Source Data Store. Converted Data and its associated Vital Data are sent to the System Output. The System Output is compatible with downstream data analysis tools. Therefore, once an event or trigger occurs it is marked; thus the system can determine if source data ever had a problem because it had been marked previously. A Vital Data file is associated with source data so that source data can be further explored. Also, the system can examine a data signature profile.

Figure 3A:
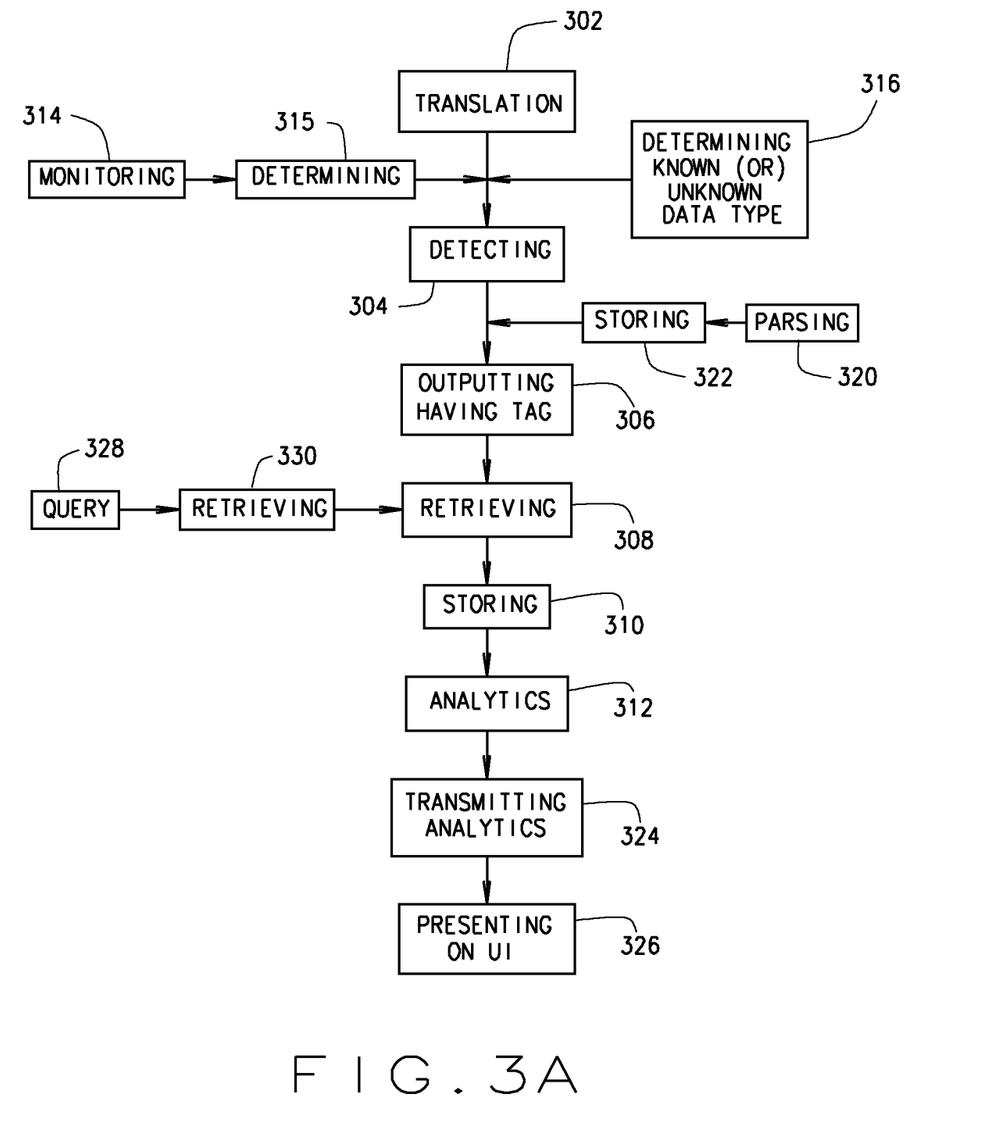
FIG. 3A is a flow diagram for illustrating the data processing.

Referring to FIG. 3A, an illustrative flow diagram of the method 300 for processing source data is provided. The process includes, translating 302 with a translation processor a stream of source data received into a stream of formatted data types based on one or more of parameter definitions for the source data and new parameter information for the source data having an unknown data type. The process further includes, detecting 304 with a vital data processor event data associated with a trigger and outputting it 306 to a database. It will also capture data surrounding the event and tag it as vital data associated to the event. The process can also include, performing associated data analytics and diagnosis, introspection, prediction and prognosis.

In yet another implementation of the technology as disclosed, the method for processing source data can include parsing 320 and storing 322 the stream of source data in the database based on logical types using a parsing processor configured on the server. The data is parsed based on some logical criteria that fits the data. For example, source data for flights can contain more than 1 flight—legs. The system will logically parse out the source data into flight-legs. The process can further include transmitting 324 analytic results from the server to a workstation where the analytic results include one or more of trend data analytic results, associated data analytic results and preventative action analytic results, and presenting 326 the analytic results on a user interface of the workstation. The process can provide for querying 328 and retrieving 330 from the database the tagged event data and the surrounding trigger data.

Figure 3B:
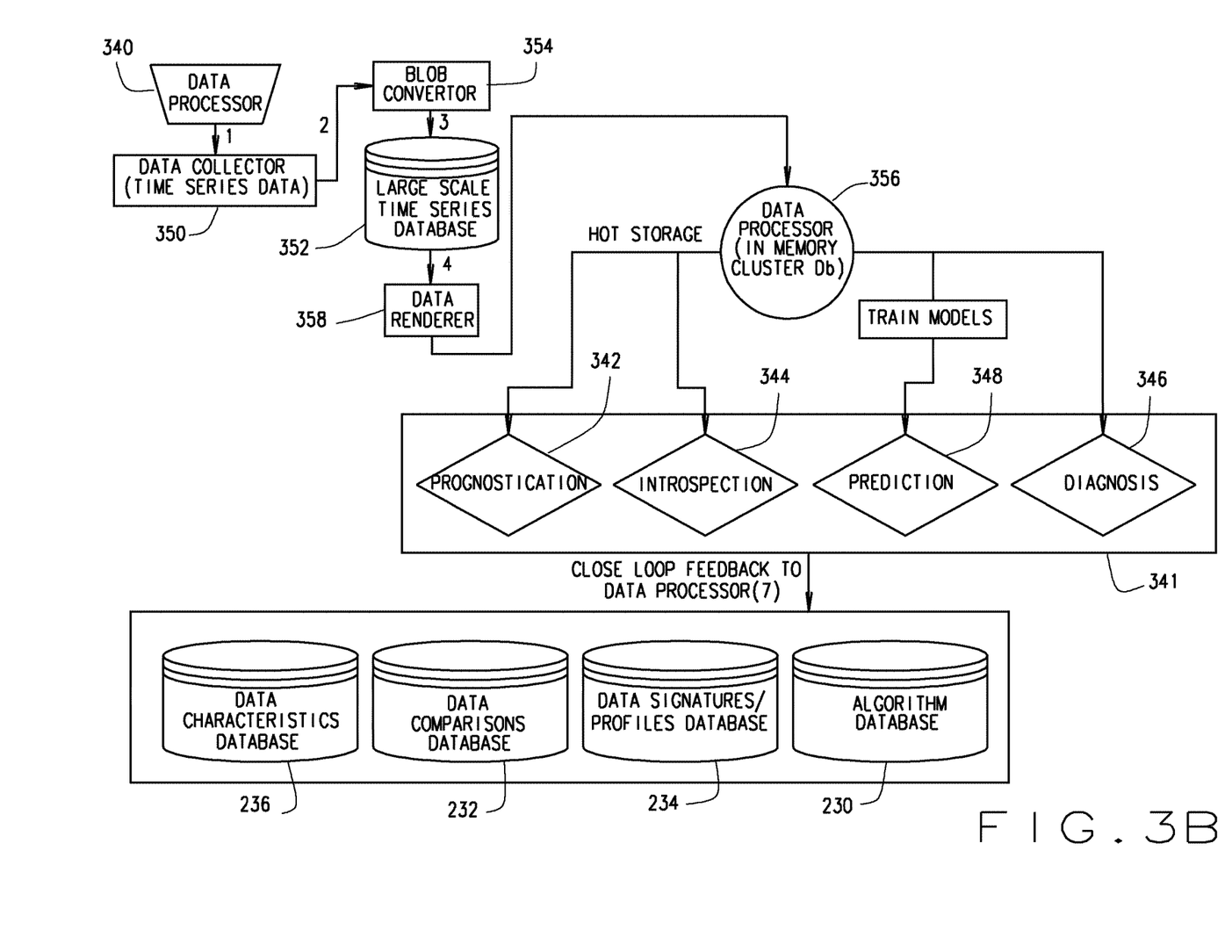
FIG. 3B is a flow diagram illustrating the data analytics.

Referring to FIG. 3B, an illustration of the Data Analytics flow is provided. Large scale data analytics, tools and processing components 122 is responsible for analyzing the source data provided by the data processor 340. This data analytics processor component 340 includes advanced analysis methods 341 including prognostication 342, introspection 344, diagnosis 346 and prediction 348 algorithms. The advanced analysis methods can use a summary of the source data rather than the entirety of the source data. The data processor 340 component 340 is responsible for aggregating source data, and converting data. An aggregation function including one or more of averaging, maximizing, summing and minimizing can be used to reduce the amount of data provided to the analytics algorithms. Source data can also be grouped together to reduce the data returned. The converting function can reformat the source data provided, which may not be in the format needed for the data collector to consume. For example, the source data may be grouped by frequency, whereas at other times the source data may come in wide format where each parameter name is a column name. The data processor 340 can be responsible for converting incoming data into a format that the data collector can consume. The final data output provided by this data analytics processor component 340 is used by the data collector.

The data collector 350 is a high performance component for loading the time series database with source data. The data collector 350 is optimized for rapid ingestion of source data. The data collector includes several modes for loading data including support for direct data loader, file loader and application program interfaces (APIs). The data collector component [340] can expose a REST API. The analytics data processor has an option to invoke the data collector using the API rather than using a file loader. The REST API can be used when a small set of current source data is being collected. However, a file loader function can be used in most cases. Source data collected is stored in a large scale time series database 352 like Apache HBASE. It can rapidly ingest and store source data provided by the data collector to a database electronic memory such as a memory disk. The Blob Convertor component 354 can convert the source data into a compressed blob format before it is stored in the time series database 352. Source data is converted into blob format for storage efficiency. The blob Convertor 354 can be functionally integrated and coupled between the data collector 350 and the large scale time series database 352 so that the source data can be converted to blob in memory before it is stored to the time series database electronic memory (disk).

A data renderer component can be responsible for converting the blob data back into America Standard Code for Information Interchange (ASCII) data. The data renderer component can include functionality selectively retrieving and providing data from a selected time series database 352. Compressed binary source data stored in the time series database can be un-compressed and converted back to ASCII so that the uncompressed data can be used by advanced analytic methods 341. For example, tools and algorithms for advanced analytics can require ASCII. The data required can be identified by using a time series name, a date/time range and a parameter name. The data renderer can also include functionality for down sampling where the time series data can be stored in the database at a much higher frequency. The data renderer will down sample the data to lower frequency for downstream computing systems to consume. The data renderer component can also include functionality for aggregating, where the time series data is aggregated using one or more functions an average, a sum, and a minimum. The data renderer component can also include functionality for interpolating, where the data renderer component will regularize data returned by interpolating data as desired to particular standard intervals. It ensures data is available at all intervals, which facilitates use with advanced analytic algorithms and makes the data more conducive for generating, presenting, and displaying charts and graphs for data analytics.

The analytics system can leverage an in-memory data processor computing system 356 to process time series data. The in-memory data processor computing system (like Apache Spark) can be optimized for processing large scale time series data for analytics. Specifically, the in-memory data processor computing system can implement logic related to prognostication (use cases related to short- and long-term trends for selected source data measurement), introspection (use cases related to correlating source data measurements over a period of time), prediction (use cases related to developing machine learning) and diagnosis (Use cases related to identifying measurements that might indicate the cause of events like component failures). Predictive analytics can be based on Machine Learning techniques. Machine Learning problems typically require a sample of data used to derive a model. The derived model can then be used to predict characteristics of unknown data. In one implementation, Prognostication 342, Introspection 344 and Diagnosis 346 can based on statistics and optimization; and Prediction 348 can be based on machine learning.

The various implementations and examples shown above illustrate a method and system for processing source data and performing analytics. A user of the present method and system may choose any of the above implementations, or an equivalent thereof, depending upon the desired application. In this regard, it is recognized that various forms of the subject data processing and data analytic method and system could be utilized without departing from the scope of the implementations as disclosed As is evident from the foregoing description, certain aspects of the present implementation as disclosed are not limited by the particular details of the examples illustrated herein, and it is therefore contemplated that other modifications and applications, or equivalents thereof, will occur to those skilled in the art. By way of illustration various processors may be combined, for example the vital processor and data processors can be combined or further subdivided functionally without departing from the scope of the technology as disclosed. By way of further illustration, the databases may be combined or further subdivided. It is accordingly intended that the claims shall cover all such modifications and applications that do not depart from the scope of the present implementation. Accordingly, the specification and drawings are to be regarded in an illustrative rather than a restrictive sense.

Certain systems, apparatus, applications or processes are described herein as including a number of modules (components or functions). A module may be a unit of distinct functionality that may be presented in software, hardware, or combinations thereof. When the functionality of a module is performed in any part through software, the module includes a computer-readable medium. The modules may be regarded as being communicatively coupled. The inventive subject matter may be represented in a variety of different implementations of which there are many possible permutations. By way of illustration, the database query function 134 and the comparator function 136 may be a unit of distinct functionality that may be presented in software, hardware, or combinations thereof.

The methods described herein do not have to be executed in the order described, or in any particular order. Moreover, various activities described with respect to the methods identified herein can be executed in serial or parallel fashion. In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine or computing device. Further, while only a single machine is illustrated, the term "machine" shall also be taken to include any collection of machines that individually or jointly execute a set (or multiple sets) of instructions to perform any one or more of the methodologies discussed herein.

The computer systems or servers and client computers as disclosed can include a processor (e.g., a central processing unit (CPU) a graphics processing unit (GPU) or both), a main memory and a static memory, which communicate with each other via a bus. The computer system may further include a video/graphical display unit (e.g., a liquid crystal display (LCD) or a cathode ray tube (CRT)). The computer system and client computing devices, can also include an alphanumeric input device (e.g., a keyboard), a cursor control device (e.g., a mouse), a drive unit, a signal generation device (e.g., a speaker) and a network interface device. An illustrative example of these type of computing devices include the user workstations.

The drive unit includes a computer-readable medium on which is stored one or more sets of instructions (e.g., software) embodying any one or more of the methodologies or systems described herein. The software may also reside, completely or at least partially, within the main memory and/or within the processor during execution thereof by the computer system, the main memory and the processor also constituting computer-readable media. The software may further be transmitted or received over a network via the network interface device.

The term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present implementation. The term "computer-readable medium" shall accordingly be taken to include, but not be limited to, solid-state memories, and optical media, and magnetic media.

The various implementation and examples of the technology as disclosed and shown above illustrate a system and method for data processing and data analytics. A user of the present invention may choose any of the above implementations as disclosed, or an equivalent thereof, depending upon the desired application. In this regard, it is recognized that various forms of the subject technology as disclosed could be utilized without departing from the scope of the technology as disclosed and its various implementations.

As is evident from the foregoing description, certain aspects of the present invention are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the sprit and scope of the present invention.

Other aspects, objects and advantages of the present invention can be obtained from a study of the drawings, the disclosure and the appended claims.

What is claimed is:

1. A computer system for processing large scale source data, comprising:
   a hardware monitor processor configured to monitor a stream of source data received at the computer system from a variety of sources of sensor data from one or more aircraft sensors and determine a data type for each source data in the stream of source data;
   a master conversion database configured with definitions and a database query function and a comparator that determines if data contained in the stream of source data is of a known data type or an unknown data type based on a comparison with the definitions, wherein the unknown data type is from a new data source that has not been previously recorded;
   a hardware translation processor configured to translate the stream of source data into a stream of formatted data based on one or more of definitions for the source data;
   a hardware data conversion processor configured to configure a data definitions database with a new definition to detect the unknown data type and merge the new definition with the master conversion database;
   a hardware vital data processor configured to input the stream of formatted data contained in the stream of source data into a dataset database by using an algorithm that identifies vital data using a conversion data map as a key, a data characteristic that identifies vital data using one of a plurality of characteristics of the source data, or a data signature that identifies vital data using a signature of the source data, and to process a trigger function, which detects formatted data associated with a trigger event associated with a physical trigger event that is representative of a physical system that is operating outside of a normal range and outputs, to the dataset database, event data as a vital data parameter that is out of tolerance, the event data being tagged to produce a tagged event data having a tag associated with the source data and the trigger event and retrieves and stores surrounding data associated with the trigger event and having a predetermined relationship to the trigger event to the dataset database; and
   a hardware data analytics processor configured to perform one or more of diagnosis, introspection, prediction and prognosis analytics based on the tagged event data and the surrounding data.

2. The computer system for processing source data as recited in claim 1, wherein the hardware monitor processor is further configured to determine a manner in which the data can be stored and an operation to be performed on the source data and the data definition database provides new information for unknown data type to build the conversion data map.

3. The computer system for processing source data as recited in claim 2, further comprising: a hardware data parsing processor configured to parse and store the stream of source data in the dataset database.

4. The computer system for processing source data as recited in claim 3, further comprising: a computer workstation receiving analytic results including one or more of trend data analytic results, associated data analytic results and preventative action analytic results having a user interface, which displays the analytic results in a user readable format.

5. The computer system for processing source data as recited in claim 4, further comprising: a hardware data query processor configured to query and retrieve from the dataset database surrounding data related to the trigger event and associated to the stream of source data.

6. The computer system for processing source data as recited in claim 1, where the hardware data analytics processor comprises an advanced analytic method including one or more of prognostication, introspection, diagnosis and prediction algorithms, whereby the hardware data analytics processor aggregates source data, converts source data into a compressed binary format for storage in a time series database.

7. The computer system for processing source data as recited in claim 6, further comprising: a data renderer selectively retrieving and providing uncompressed data from selected time series in America Standard Code for Information Interchange (ASCII) format, wherein the uncompressed data that is retrieved is identified based on a time series name and a tag and value pair.

8. The computer system for processing source data as recited in claim 7, where the data renderer down samples compressed sourced data from the time series database at a lower frequency as compared to a higher frequency of stored converted source data.

9. The computer system for processing source data as recited in claim 7, where the data renderer aggregates compressed source data in the time series database by one or more functions including averaging, summing and minimizing.

10. The computer system for processing source data as recited as claim 7, where the data renderer regularizes compressed source data by interpolating the compressed source data.

11. A computer-implemented method for processing source data, comprising:
    monitoring, with a hardware monitor processor, a stream of source data received at a computer system from a variety of sources of sensor data from one or more aircraft sensors and determining a data type for each source data in the stream of source data;
    configuring a master conversion database with definitions and a database query function and a comparator that determines if data contained in the stream of source data is of a known data type or an unknown data type based on a comparison with the definitions, wherein the unknown data type is from a new data source that has not been previously recorded;

translating, at the computer system with a hardware translation processor, the stream of source data into a stream of formatted data based on the master conversion database and a data definitions database for the source data with known and unknown data;

detecting, with a hardware data conversion processor at a computer server, the unknown data type and configuring the data definitions database with a new definition to detect the unknown data type detecting, with a hardware vital data processor at the computer server using an algorithm that identifies vital data using a conversion data map as a key, a data characteristic that identifies vital data using one of a plurality of characteristics of the source data, or a data signature that identifies vital data using a signature of the source data, data associated with a trigger event associated with a physical trigger event that is representative of a physical system that is operating outside of a normal range and outputting, to a dataset database, event data as a vital data parameter that is out of tolerance, the event data being tagged to produce a tagged event data having a tag associated with source data and the trigger event and retrieving and storing surrounding data associated with the trigger event to the dataset database; and performing, on the data type, one or more of trend data analytics, associated data analytics and preventative action analytics.

12. The computer-implemented method for processing source data as recited in claim 11, wherein the monitoring determines a manner in which the data can be stored and an operation to be performed on the source data and the detecting the unknown data type comprises building the conversion data map where the data definition database is configured with new information for the unknown data type.

13. The computer-implemented method for processing source data as recited in claim 12, comprising: parsing and storing the stream of source data in the dataset database using a parsing processor configured on the computer system wherein the data is parsed based on a predetermined criteria.

14. The computer-implemented method for processing source data as recited in claim 13, comprising: transmitting analytic results from the computer system to a workstation where the analytic results include one or more of trend data analytic results, associated data analytic results and preventative action analytic results; and presenting the analytic results on a user interface of the workstation.

15. The computer-implemented method for processing source data as recited in claim 14, comprising: querying and retrieving from the dataset database surrounding data.

16. The computer-implemented method for processing source data as recited in claim 11, further comprising: one or more of prognosticating, introspectioning, diagnosing and predicting algorithms; aggregating source data; and converting source data into a compressed binary format for storage in a time series database.

17. The computer-implemented method for processing source data as recited in claim 16, further comprising: a data renderer selectively retrieving and providing uncompressed source data from a selected time series database by identifying data based on a time series name and a tag and value pair.

18. The computer-implemented method for processing source data as recited in claim 17, where the data renderer down samples compressed sourced data from the time series database at a lower frequency as compared to a higher frequency of stored converted source data.

19. The computer-implemented method for processing source data as recited in claim 17, where the data renderer aggregates compressed source data in the time series database by one or more functions including averaging, summing and minimizing.

20. The computer-implemented method for processing source data as recited as claim 17, where the data renderer will regularize compressed source data interpolating the compressed source data.

* * * * *